United States Patent [19]

Williams

[11] Plant 4,755

[45] Jul. 28, 1981

[54] MINIATURE ROSE PLANT

[76] Inventor: Ernest D. Williams, 1510 Lebanon Ave., Dallas, Tex. 75208

[21] Appl. No.: 145,782

[22] Filed: May 1, 1980

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the multi-color buds and flowers of yellow blended with pink, orange and scarlet and by the profusion of bloom.

1 Drawing Figure

1

The present invention relates to a new and distinct variety of hardy, dwarf, bush type rose plant of the miniature class; the variety being primarily characterized — as to novelty — by the multi-color buds and flowers of yellow blended with pink, orange and scarlet, which in general color effect are similar to Circus, a Floribunda variety (U.S. Plant Pat. No. 1,382, expired).

The variety is further characterized by:

An abundance of bloom, with flowers usually borne singly on sturdy, slender stems.

Sweet light fragrance.

A plant which is vigorous, of rounded somewhat upright shape with firm glossy, small foliage with pointed leaflets; the buds and flowers being similar in form but slightly larger in size to Over the Rainbow (Miniature — U.S. Plant Pat. No. 3,472).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between an un-named seedling, as the seed parent and Over the Rainbow (miniature — U.S. Plant Pat. No. 3,472), as the pollen parent.

Subsequent to origination of the variety I successfully reproduced it, at my nursery located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

Variety name: Sarajean.

Flowers borne: Usually singly on slender wirey stems.

Quantity of bloom: Abundant both outside and in greenhouse.

2

Bud:

*Peduncle.*—Medium length; slender but sturdy; erect; medium green, sometimes tinted bronze (outdoors); Hairs — few or none.

*Before calyx breaks.*—Size — small. Form — medium long, pointed with some foliaceous appendages and few or no tiny hairs on surface of bud; with foliaceous parts extending beyond the tip of the bud equal to one-half or more of its length. Color — medium green, occasionally tinted with bronze (outdoors).

*As calyx breaks.*—Color — red — over yellow. Opening: opens well in all weather.

Bloom:

*Size when fully open.*—Small, averaging about 30 mm ($1\frac{1}{4}''$).

*Petalage.*—Double — averaging about 50 petals, arranged regularly plus sometimes several small petaloids.

*Form.*—Globular at first, becoming more open in the center, with petals reflexing loosely outward, and later at maturity, open and rolled loosely outward, and downward. Open flowers may show stamens.

Petals: Fairly thick; satinly on inside and on outside surface.

*Shape.*—Outside petals, broad lanceolate (almost round) with rounded tip; intermediate — broad lanceolate with rounded tip; inside — lanceolate with rounded tip.

Color: Newly opened flower from a plant grown (Apr. 1980), Dallas, Tex.:

*Outside petal.*—Outside surface — near Buttercup Yellow 5/3 (sometimes darker), often brushed or overlaid down center of petal with red or orange, the exact color depending upon intensity of underlying yellow and of the overlay of red (this is determined to great extent by light intensity and can vary from flower to flower and time of year. Inside surface — near Buttercup Yellow 5/3 (may be lighter or darker yellow, as above) with the tip $\frac{1}{4}$ or more of petal tinted or overlaid with red (near Mandarin Red 17/2) of varying intensity, depending upon sunlight and weather conditions. Note: as petals mature/age (see color illustration) the red becomes darker (approaching Currant Red 821/1) but modified by the underlying color which becomes near white.

*Intermediate petal.*—Outside surface — similar to outside petal, but more yellow (near Buttercup Yellow 5/3 — may be darker or lighter) area with only a slight tint of orange or red. Inside surface — similar to outside petal — but with less of the red or orange shading.

*Inner petal.*—Outside surface — similar to intermediate petal; inside surface — similar to intermediate petal. General color effect; newly opened flower — yellow to peach pink with outer edge (petal tip) tinted with red. Three days open — color similar to newly opened flowers but yellow area becoming more peach to red in color. Behavior — opens well in all weather. Color lasts well even in hot weather. Red coloring most pronounced in full sunlight (outdoors) — more yellow and pink in greenhouse. Spent petals drop off. Flower longevity (April 1980) — plant in pot 6–8 days or longer. Cut flowers at living room temperature 4–5 days or longer.

Reproductive organs:

*Stamens.*—Few; arranged regularly about pistils.

*Filaments.*—Varying length, fairly short, yellow.

*Anthers.*—Some not well formed; yellow.

*Pollen.*—Little or none.

*Pistils.*—Average number.

*Styles.*—Fairly even; medium to short length; bunched; color — reddish.

*Ovaries.*—All enclosed in calyx.

*Hips.*—Few or none.

*Sepals.*—Permanent; spear shaped; recurved against peduncle.

*Seed.*—None.

Foliage:

*Leaves.*—Compound of five (sometimes three or seven) leaflets; fairly small; leathery; glossy.

*Leaflets.*—Shape: broad, nearly oval; apex acute; base rounded. Margin serrate. Color: dark green to bronzy; new growth — normal (medium) green. Rachis: medium strength; upper side may have a few tiny short prickles or hairs, grooved. Underside — several small hooked thorns with few or no tiny prickles. Stipules: medium long; narrow to medium width; medium length; narrow points which turn out usually at about 45 degrees or more.

Growth:

*Habit.*—Dwarf; bushy; upright; much branched.

*Growth.*—Free vigorous; internodes short.

*Canes.*—Medium; slender; sturdy.

*Main stems.*—Color: medium green.

*Thorns.*—Average; slender; nearly straight, inclined slightly downward; color; brown (tan). Prickles — none. Hairs — none.

*Branches.*—Color: medium green. Thorns: moderate number; medium length; slender; nearly straight, inclined downward. Medium oval base. Prickles: none. Hairs — none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of a rich blend of yellow, peach pink, orange and red, the bud and flower resembling the variety Circus (U.S. Plant Pat. No. 1,382, expired) in color and resembling the variety Over the Rainbow in form and size; and further characterized by a plant of vigorous and compact growth habit, easy to propagate from cuttings or by budding, with an abundance of small to medium size glossy foliage and an abundance of flowers borne usually singly on sturdy wirey stems.

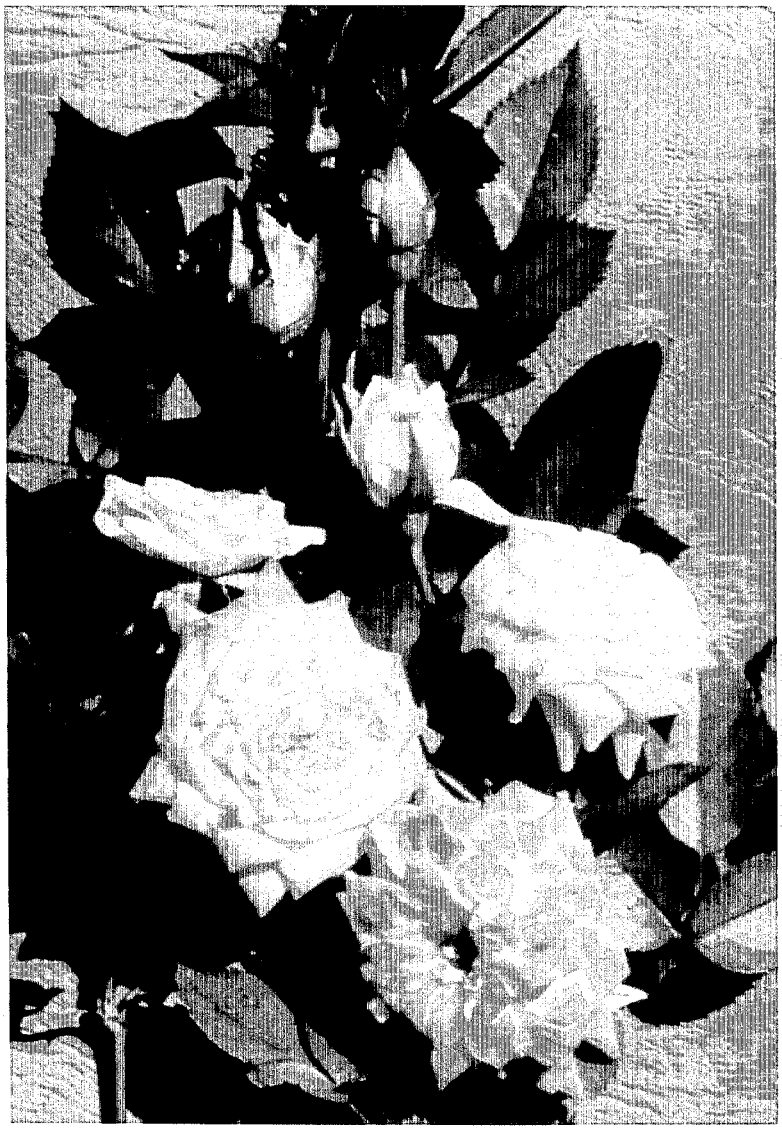

* * * * *